US009878020B2

United States Patent
Mateescu et al.

(10) Patent No.: US 9,878,020 B2
(45) Date of Patent: Jan. 30, 2018

(54) ORAL ENZYME COMPOSITIONS FOR INTESTINAL DELIVERY

(75) Inventors: Mircea-Alexandru Mateescu, Montréal (CA); Carmen Calinescu, Pierrefonds (CA); Pompilia Ispas-Szabo, Longueuil (CA); Bruno Mondovi, Rome (IT); Rodolfo Federico, Rome (IT)

(73) Assignee: Histapharm Inc., Montreal (CA)

( * ) Notice: Subject to any disclaimer, the term of this patent is extended or adjusted under 35 U.S.C. 154(b) by 295 days.

(21) Appl. No.: 14/110,431

(22) PCT Filed: Apr. 5, 2012

(86) PCT No.: PCT/CA2012/000352
§ 371 (c)(1),
(2), (4) Date: Apr. 9, 2014

(87) PCT Pub. No.: WO2012/135951
PCT Pub. Date: Oct. 11, 2012

(65) Prior Publication Data
US 2014/0212492 A1    Jul. 31, 2014

Related U.S. Application Data

(60) Provisional application No. 61/472,726, filed on Apr. 7, 2011.

(51) Int. Cl.
*A61K 38/44* (2006.01)
*A61K 9/20* (2006.01)
(Continued)

(52) U.S. Cl.
CPC .............. *A61K 38/44* (2013.01); *A61K 9/205* (2013.01); *A61K 9/2059* (2013.01); *A61K 36/48* (2013.01);
(Continued)

(58) Field of Classification Search
CPC ........ A61K 38/43; A61K 38/44; A61K 38/54; A61K 9/2059; A61K 9/2054; A61K 9/205;
(Continued)

(56) References Cited

U.S. PATENT DOCUMENTS 6,005,090 A * 12/1999 Doidge ................ C12N 9/0065
435/7.32
2003/0091552 A1* 5/2003 Cartwright .............. A23L 33/18
424/94.4
(Continued)

FOREIGN PATENT DOCUMENTS

CA    2571463    12/2006

OTHER PUBLICATIONS

Barynin et al. Crystal structure of manganese catalase from Lactobacillus plantarum. Structure vol. 9,725-738, Aug. 2001.*
(Continued)

*Primary Examiner* — Lakshmi S Channavajjala
(74) *Attorney, Agent, or Firm* — Klauber & Jackson LLC (57) ABSTRACT

The present disclosure describes compositions for intestinal delivery of enzyme formulations and methods of treating health problems with these formulations. More specifically, the enzyme formulations include at least one histaminase and various methods of treatment of physical conditions, such as inflammation, allergy, histamine intolerance, and intestinal cancer.

14 Claims, 7 Drawing Sheets

(51) Int. Cl.
*A61K 45/06* (2006.01)
*A61K 36/48* (2006.01)

(52) U.S. Cl.
CPC ...... *A61K 45/06* (2013.01); *C12Y 104/03022* (2013.01)

(58) Field of Classification Search
CPC ... A61K 9/20; A61K 36/44; C12Y 104/03022
See application file for complete search history.

(56) References Cited

U.S. PATENT DOCUMENTS

| | | | |
|---|---|---|---|
| 2005/0226905 A1* | 10/2005 | Tien ..................... | A61K 9/0024 424/439 |
| 2007/0184118 A1* | 8/2007 | Li ........................ | A61K 9/1652 424/489 |
| 2008/0102114 A1* | 5/2008 | Koritala ............... | A61K 9/1652 424/456 |
| 2008/0193491 A1 | 8/2008 | Missbichler et al. | |
| 2008/0279840 A1 | 11/2008 | Mondovi et al. | |
| 2012/0252833 A1* | 10/2012 | Wertz ................... | A61K 9/2013 514/289 |
| 2013/0195830 A1* | 8/2013 | Sipka .................... | A61K 36/48 424/94.4 |

OTHER PUBLICATIONS

Takka et al. Evaluation of Chitosan/Alginate Beads Using Experimental Design: Formulation and In Vitro Characterization. AAPS PharmSci Tech vol. 11, No. 1, Mar. 2010 pp. 460-466.*
XP-002631128 Abstract Biro, T et al (2010) Pepsin and Trypsin resistant-food complement preparation comprises histaminase of vegetable origin, catalase and protease inhibitor WPI/Thomson vol., 2011 No. 4.
Database Embase XP00273058 Database Accession No. EMB-0007003603 abstract Goldberg, LG (1940) Histaminase in the treatment of allergic dermatoses JAMA vol. 115 No. 6 pp. 429-432 ISSN: 0098-7484.
Leblanc, JG et al (2011) Use of superoxide dismutase and catalase producing lactic acid bacteria in TNBS induced Crohn's disease in mice Journal of Biotechnology 151(3):287-293.
Saboktakin, MR et al (2011) Synthesis and in vitro evaluation of carboxymethyl starch-chitosan nanoparticles as drug delivery system to the colon Internatl Journ of Bio Macromolecules 48(3):387-385.
Assaad, et al., Carbohydrate Polymers, "Polyelectrolyte complex of carboxymethyl starch and chitosan as drug carrier for oral administration," 2011; 84: 1399-1407.
Calinescu, et al., Eur J. Pharm Biopharm, "Carboxymethyl high amylose starch: Chitosan self-stabilized matrix for probiotic colon delivery," 2008; 70(2): 582-9.
Calinescu, "Matrices à base de carboxyméthyl amidon pour des formulations pharmaceutiques d'agents bioactifs à administration orale," Ph.D. Thesis, Université du Québec à Montréal. http://www,archipel.uqam.ca/3973/I/D2126.pdf 2011 (copyright Feb.). *see pp. 185 to 215*.
PCT/International Search Report (ISR)—PCT/CA2012/000352(Form PCT/ISA/210) —dated Aug. 2, 2012—3 pages.
D'Agostino, et al., Gut, "Postheparin plasma diamine oxidase values in the follow up of patients with small bowel Crohn's disease," 1991; 32: 932-5.
Federico, et al., Inflamm Res., "Immobilization of plant histaminase for medical applications," 2000; 49(Suppl 1): S60-1—Abstract.
Federico, et al., J Control Release, "Histaminase PEGylation: preparation and characterization of a new bioconjugate for therapeutic application," 2006; 115: 168-74—Abstract.
Fogel, et al., Inflamm. Res., "The effect of diamine oxidase administration on experimental ulcerative colitis in rats," 2006, 55(Suppl 1): S63-S64—Abstract.
Hilsden, et al., Inflamm Bowel Dis., "Intestinal permeability and postheparin plasma diamine oxidase activity in the prediction of Crohn's disease relapse," 1999; 5: 85-91.
Honzawa, et al., Inflamm Bowel Dis., "Clinical significance of serum diamine oxidase activity in inflammatory bowel disease: Importance of evaluation of small intestinal permeability," 2011; 17(2): E23-5.
Masini, et al., Scientific World Journal, "Pea seedling histaminase as a novel therapeutic approach to anaphylactic and inflammatory disorders. A plant histaminase in allergic asthma and ischemic shock," 2007; 7: 888-902.
Masini, et al., Biochem Biophys Res Commun, "Protective effects of a plant histaminase in myocardial ischaemia and reperfusion injury in vivo," 2003; 309: 432-9—Abstract.
Masini, et al., Eur J Pharmacol., "Effect of a plant histaminase on asthmalike reaction induced by inhaled antigen in sensitized guinea pig," 2004; 502: 253-64—Abstract.
Schmidt, et al., Agents Actions, "Human intestinal diamine oxidase (DAO) activity in Crohn's disease: a new marker for disease assessment?" 1990; 30: 267-70—Abstract.
Thompson, et al., Am J Gastroenterol, "Intestinal mucosa diamine oxidase activity reflects intestinal involvement in Crohn's disease," 1988; 83: 756-60—Abstract.
Fogel, et al., "Copper Amine Oxidases in Intestine Diseases, Book chapter in Copper Amine Oxidases: Structures, Catalytic Mechanisms and Role in Pathophysiolog,"y (G Floris,and B Mondovi, eds), CRC-Press (USA) 2009.

* cited by examiner

ORAL ENZYME COMPOSITIONS FOR INTESTINAL DELIVERY

CROSS-REFERENCE TO RELATED APPLICATIONS

This application is a U.S. National Phase application under 35 USC §371 of PCT/CA2012/000352, filed Apr. 5, 2012, which in turn, claims priority from and the benefit of U.S. Provisional Application No. 61/472,726, filed Apr. 7, 2011. Applicant claims the benefits of 35 U.S.C. '120 as to the PCT application and priority under 35 U.S.C. '119 as to the said United States provisional application, and the entire disclosures of both applications are incorporated herein by reference in their entireties.

BACKGROUND (a) Field

The subject matter disclosed generally relates to oral enzymatic compositions for the treatment of various intestinal diseases.

(b) Related Prior Art

The diamine oxidase (EC 1.4.3.6), also called histaminase, catalyses oxidative deamination of histamine and other biogenic amines, with the release of the corresponding aldehydes, hydrogen peroxide ($H_2O_2$) and ammonia ($NH_3$). As previously shown with other copper oxidases, such as ceruloplasmin and bovine serum amine oxidase, with anti-oxidant properties, diamine oxidase (DAO) of vegetal origin (VDAO), with an enzymatic activity higher than that of the animal DAO, presents some beneficial effects in ischemia and reperfusion injury. Plant histaminase also exhibits a beneficial effect in an anaphylactic response. Furthermore, it was also proposed for the treatment of asthma-like reaction. Recently, it was shown that pea seedling DAO, parenterally administered, may have protective effects on intestinal ischemia, by reducing local tissue inflammation through acceleration of histamine catabolism and by preventing free radical-mediated tissue injury, with significant decrease in tissue levels of peroxidation and nitration products, of DNA damage and of ileal cell apoptosis.

The DAO is also the main histamine degrading enzyme acting predominantly in the intestinal tract. The presence of DAO in the intestinal mucosa may induce a protection against the endogenous or exogenous (food) histamine. The enhancement of histamine content in human could be imputable to various factors. Food-induced histaminosis can generate plasma histamine elevation and haemodynamic alterations, particularly when associated with low DAO activity. A high histamine content in some food can become toxic, especially in certain oriental food. Elevated histamine content in food and beverages can also be associated to microbial contamination. The mechanism of pseudo-allergic reactions of histamine caused by food seems to be mainly ascribed to an intestinal hyperpermeability (caused by irritant species such as alcohol) or by decrease of DAO enzymatic activity. Since DAO is a major catabolic enzyme for histamine in humans, its lower mucosal level at the sites of inflammation would generate an accumulation of the released histamine, which may participate to the induction and enhancement of acute inflammatory responses. Thus, in the pathogenesis of inflammatory bowel diseases (IBD), mucosal alterations are frequently reflected in changes of mucosal DAO activity and, respectively, in mucosal histamine content. Lower tissues levels of DAO activity were found in areas of macroscopically-inflamed tissue in IBD than in normal tissues. The jejunal secretion of histamine was reported as higher in Crohn's disease and was significantly correlated with the Crohn's disease activity index. High histamine content was also found in experimental neoplasias, such as colon carcinomas.

Another factor involved in the pathogenesis of intestinal inflammation is the oxidative stress that can amplify the intestinal inflammation by increasing mucosal and vascular permeability and by recruitment and activation of more neutrophils, with higher release of free radicals and pro-oxidant species. An important component of the endogenous defense against oxidative stress is represented by antioxidant enzymes, such as intracellular superoxide dismutase, catalase, glutathione peroxidase or circulatory ceruloplasmin. Decreased antioxidant enzyme activities or an unbalanced expression of one of these enzymes may increase the vulnerability of cells to reactive oxygen species, hindering recovery of the mucosa, as reported in IBD (Buffinton and Doe, *Free Radic Biol Med* 1995; 19: 911-918). Thus, to compensate the loss of antioxidant defense, treatments with antioxidants are requested.

Concerning the therapeutically effects of DAO on IBD, Fogel and Lewinski (*Inflamm Res* 2006; 55: S63-S64) showed a possible therapeutic effect of hog kidney DAO, administrated intra-peritoneally, on a model of ulcerative colitis (UC) in rat, with a reduction of inflammatory reaction. Decreasing the histamine levels and preventing the oxidative stress in intestinal inflammation could be a promising bi-functional therapeutic strategy to better manage the IBD. As for most of oxidases, a by-product of the DAO enzymatic reaction is $H_2O_2$, a pro-oxidant agent which can present desirable bactericidal and undesirable oxidative damaging effects. Catalase (EC 1.11.1.6) is an anti-oxidant enzyme that specifically catalyzes the decomposition of $H_2O_2$. Due to its capacity to decompose $H_2O_2$, catalase was proposed for use in post-ischemic reperfusion injury in myocardial infarction and stroke, burns, trauma, renal transplants, respiratory distress syndrome and broncho-pulmonary displasia (U.S. Pat. No. 5,334,382 to Phillips and Snow) as parenteral formulations of the enzyme covalently bound to polyethylene glycol.

Delivery of bioactive agents to upper intestine and/or colon without gastric or intestinal degradation during the gastro-intestinal transit of the oral dosages represents a major challenge. In this context, the design of biodegradable intestinal delivery systems of bioactive agents for different diseases, such as colon cancer, IBD including Crohn's disease and Ulcerative Colitis, gained increasing interest. Such therapeutic forms that target intestinal sites could improve the treatment of these diseases. As colonic microflora produces a large number of degrading enzymes, several natural polysaccharides from algal (alginates), plant (pectin, guar gum), microbial (dextran, xanthan gum) or animal origin (chondroitin), have been investigated as carriers for colon-specific drug delivery. In addition, colonic delivery could be achieved using pH-dependent matrices or swelling controlled systems. However, when orally administered, therapeutic proteins for intestinal targeting are susceptible to degradation during gastric and intestinal transit. In the stomach, the proteins are affected by acidic and pepsinolytic degradation, whereas in upper intestine, pancreatic and intestinal proteases also generate massive degradation of proteins. Prior art describes various functional coatings based on Eudragit® or pectin excipients formulated as beads or granulates. For example, in US 20080124279, there is proposed a colonic delivery using Zn/pectin beads protected by a functional coating. There is a continuous need to formulate and to orally administrate therapeutic proteins aimed to treat histamine-related dysfunctions.

SUMMARY

According to an embodiment, there is provided a gastro-resistant solid dosage form for the oral administration of therapeutic enzymes with intestinal delivery comprising:
- a cationic polymer, an anionic polymer, or a neutral polymer, or a combination thereof; and
- at least one enzyme.

The oral solid dosage form may comprise a combination of a cationic polymer and an anionic polymer.

The enzyme may be a histaminase.

The histaminase may be a vegetal histaminase.

The vegetal histaminase may be chosen from *Pisum sativum* L. histaminase, *Lens culinaris* histaminase, *Cicer arietinum* histaminase, *Lathyrus sativus* histaminase, and mixtures thereof.

The vegetal histaminase may be a pea seedlings DAO.

The oral solid dosage form may be further comprising an anti-oxidant enzyme, and the anti-oxidant enzyme may be a catalase.

The anionic polymer may be chosen from carboxymethylcellulose, carboxymethylstarch, an alginate, a pectin, a methacrylic copolymer carrying carboxylic groups, an hydroxypropylmethylcellulose phthalate, an hydroxypropylmethylcellulose acetate succinate, or combinations thereof.

The cationic polymer may be chosen from a chitosan, a derivative of chitosan, polylysine, an aminoethyl methacrylic copolymer, or combinations thereof.

The derivative of chitosan may comprise aminoethylchitosan, tri-methylaminochitosan, or combinations thereof.

The neutral polymer may comprise a polyhydroxylic polymer.

The polyhydroxylic polymer may be chosen from hydroxypropylmethylcellulose, ethylcellulose, polyethylene oxide, a cellulose ether, or combinations thereof.

The oral solid dosage form may be uncoated.

The oral solid dosage form may be coated.

The cationic polymer and the anionic polymer may be present in a ratio of about 1:9 to about 9:1.

The cationic polymer and the anionic polymer may be present in a ratio of about 1:1.

The oral solid dosage form may be further comprising at least one bioactive agent.

The at least one bioactive agent may be at least one of a protein, a protein association, a peptide, a drug, a pro-drug, an anti-oxidant, an anti-tumoral, an anti-inflammatory, a bacteria, a probiotic, or combinations thereof.

The total amount of the enzyme in the dosage form is from about 3.3% to about 90%.

The histaminase and the anti-oxidant enzyme are present in a ratio of about 9:1 to about 1:9.

The histaminase and the anti-oxidant enzyme are present in a ratio of about 1:1 to about 2:1.

The drug may be a non-steroidal anti-inflammatory drug (NSAID).

The non-steroidal anti-inflammatory drug (NSAID) may be chosen from ibuprofen, naproxen, benoxaprofen, flurbiprofen, fenoprofen, fenbuprofen, ketoprofen, loxoprofen, pranoprofen, carprofen, oxoprofen, microprofen, tioxaprofen, suprofen, alminoprofen, fluprofen, aspirin, diflunisal, salsalate, olsalazine, sulfasalazine, indomethacin, sulindac, etodolac, ketorolac, diclofenac, mefenamic acid, meclofenamic acid, flufenamic acid, tolfenamic acid, celecoxib, valdecoxib, rofecoxib, etoricoxib or the combination thereof.

The drug may be a histamine antagonist (antihistamine).

The histamine antagonist may be chosen from a $H_1$-receptor antagonist, a $H_2$-receptor antagonist, or combination thereof.

The $H_1$-receptor antagonist may be chosen from Cetirizine, Chlorpheniramine, Clemastine, Desloratadine, Dexchlorpheniramine, Dimenhydrinate, Dimetindene, Diphenhydramine, Doxylamine, Ebastine, Embramine, Fexofenadine, Levocetirizine, Loratadine, Meclozine, Olopatadine, Pheniramine, Promethazine, Quetiapine, or combinations thereof.

The $H_2$-receptor antagonist is chosen from Cimetidine, Famotidine, Lafutidine, Nizatidine, Ranitidine, Roxatidine.

The pro-drugs may be prednisone, olsalazine, sulfasalazine.

The anti-oxidant may be chosen from vitamin C, vitamin E, a carotenoid, astaxanthin or combinations thereof.

The bacteria may be chosen from *Lactobacillus* sp., *Bifidobacterium* sp.

According to another embodiment, there is provided a method of treating a health problem comprising administering to a subject in need thereof an oral solid dosage form according to the present invention, wherein the health problem may be chosen from an enteric disease such as an ischemic colitis, an inflammatory disease, a cancer, an histamine intolerance, an allergy, a pseudo-allergic disease or combination thereof.

According to another embodiment, there is provided a method of treating an inflammatory bowel disease comprising administering to a subject in need thereof an oral solid dosage form according to the present invention.

The inflammatory bowel disease may be Crohn's disease, ulcerative colitis, collagenous colitis, lymphocytic colitis, ischemic colitis, diversion colitis, Behçet's disease, indeterminate colitis, or combination thereof.

The cancer may be intestinal cancer and/or colorectal cancer.

The allergy may be a food allergy.

According to another embodiment, there is provided an intestinal delivery composition for treating or alleviating intestinal inflammation comprising:
- a therapeutically effective amount of a histaminase enzyme and a catalase enzyme, in association with an acceptable intestinal delivery pharmaceutical formulation comprising at least one excipient as a matrix former.

The composition may be an oral dosage form.

The excipient may comprise a cationic polymer, an anionic polymer, a neutral polymer, or a combination thereof.

The anionic polymer may be chosen from carboxymethylcellulose, carboxymethylstarch, an alginate, a pectin, a methacrylic copolymer carrying carboxylic groups, an hydroxypropylmethylcellulose phthalate, an hydroxypropylmethylcellulose acetate succinate, or combinations thereof.

The cationic polymer may be chosen from a chitosan, a derivative of chitosan, polylysine, an aminoethyl methacrylic copolymer, or combinations thereof.

The derivative of chitosan may comprise aminoethylchitosan, tri-methylaminochitosan, or combinations thereof.

The neutral polymer may comprise a polyhydroxylic polymer.

The polyhydroxylic polymer may be chosen from hydroxypropylmethylcellulose, ethylcellulose, polyethylene oxide, a cellulose ether, or combinations thereof.

The cationic polymer and the anionic polymer are present in a ratio of about 1:9 to about 9:1.

The cationic polymer and the anionic polymer are present in a ratio of about 1:1.

The intestinal delivery composition may further comprise a coating.

The coating may comprise a compound chosen from hydroxypropylmethylcellulose phthalate, hydroxypropylmethylcellulose acetate succinate, ethylcellulose, and a polymethacrylate derivative.

The polymethacrylate derivative may comprise a methacrylate copolymer with carboxylic groups.

The histaminase may be a vegetal histaminase.

The vegetal histaminase may be chosen from *Pisum sativum* L. histaminase, *Lens culinaris* histaminase, *Cicer arietinum* histaminase, *Lathyrus sativus* histaminase, and mixtures thereof.

The vegetal histaminase may be a pea seedlings DAO.

The histaminase enzyme and the catalase enzyme may be present in a ratio of about 9:1 to about 1:9.

The histaminase enzyme and the catalase enzyme may be present in a ratio of about 1:1 to about 2:1.

According to another embodiment, there is provided a method of treating intestinal inflammation comprising the administration of a therapeutically effective amount of a composition according to the present invention.

The following terms are defined below.

The term "bioactive agent" is intended to mean an agent involved in the treatment of a disease, condition or health problem and this may be any kind of bioactive agents. Examples include, without limitations, proteins, drugs, such as anti-inflammatory drugs or other, prodrugs, bacteria, probiotics, antioxidants, anti-histamines.

The term "monolithic" is intended to mean a system with an unchanging and uniform structure without individual variation.

The term "histaminase" is intended to mean an enzyme which catalyses oxidative deamination of histamine and other biogenic amines. They are also called diamine oxidases (DAO).

The term "intestinal delivery" is intended to mean the delivery of bioactive agents to the intestine, which is formed by the duodenum, jejunum, ileum, ceacum, colon, rectum and anal canal, that form the small and large intestines.

The term "solid dosage form" is intended to mean any suitable physical form of a dosage, and include tablets, pills, prills, granules, pellets, beads, multiparticulates.

The term "uncoated monolithic tablet" is intended to mean a tablet with an unchanging and uniform structure (obtained by direct compression) that does not permit individual variation and does not comprise a further coating (such as an enteric coating).

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

DETAILED DESCRIPTION OF THE PREFERRED EMBODIMENTS

In embodiments, there is disclosed a bi-enzymatic composition for the treatment of intestinal diseases. According to one embodiment, CMS and Chitosan are used as co-excipients to form hydrophilic matrices (by direct compression) for the formulation of compositions and dosage forms for the delivery of enzymes. According to another embodiment, the compositions are for the delivery of enzymes in buccal, vaginal or intestinal applications. Preferably, the composition and/or dosage form are for colonic delivery of enzymes.

The preferred enzymes are histaminases, such as VDAO, and/or antioxidant enzymes, such as catalase enzymes, that may have a potential therapeutic role in the treatment of intestinal diseases.

In accordance with one embodiment, there is disclosed an oral enzymatic therapy based on the association of vegetal diamine oxidase (VDAO) with catalase for the treatment of various intestinal diseases. The VDAO would control the levels of histamine and would have some antioxidant effects. When the two enzymes are associated, catalase will eliminate the $H_2O_2$ (by-product of DAO), preventing the local intestinal oxidative stress. The association of catalase in order to decompose $H_2O_2$ produced from DAO enzymatic activity or from other inflammatory reactions is proposed herewith. Catalase will generate more oxygen ($O_2$), a substrate of VDAO, enhancing thus its efficiency (FIG. 6).

The colonic mucosa may be subjected to significant oxidative stress during inflammation related or not to histamine. It is believed that there may be an interest for new antioxidant treatments for IBD. Besides reducing local tissue inflammation through decomposition of pro-inflammatory histamine, DAO also presents some antioxidant properties, as previously shown with other copper oxidases (Mateescu et al., *J Physiol Pharmacol* 1997; 48 (Suppl. 2): 110-121; Mondovi et al., *Curr Top Med Chem* 1997; 2: 31-43; Mateescu and Nadeau, In: Floris G, Mondovi B, eds. Copper amine oxidases: structures, catalytic mechanisms, and role in pathophysiology. CRC Press, 2009: 253-260), contributing thus to counteract free radical-mediated tissue injury. In this context, the DAO is a bi-functional protein: histaminase with an amine oxidase activity controlling the level of biogenic amines, decomposing the pro-inflammatory histamine, and antioxidant, scavenging the pro-oxidant oxidative species. The vegetal histaminase (VDAO) may be a preparation from seedlings of *Pisum sativum* L., *Lens culinaris, Cicer arietinum, Lathyrus sativus*, and mixtures thereof.

Catalase, incorporated in the mono- and bi-enzymatic CMS:Chitosan formulations, reduces the amount of the hazardous $H_2O_2$, a pro-oxidant produced from DAO activity or from other inflammatory reactions. According to another embodiment, the mono-enzymatic VDAO formulation may be used for colorectal cancer therapy. According to another embodiment, the bi-enzymatic VDAO:Catalase formulations may be used for therapy for a better control of the inflammation and related deleterious effects occurred in the IBD.

Figure 6:
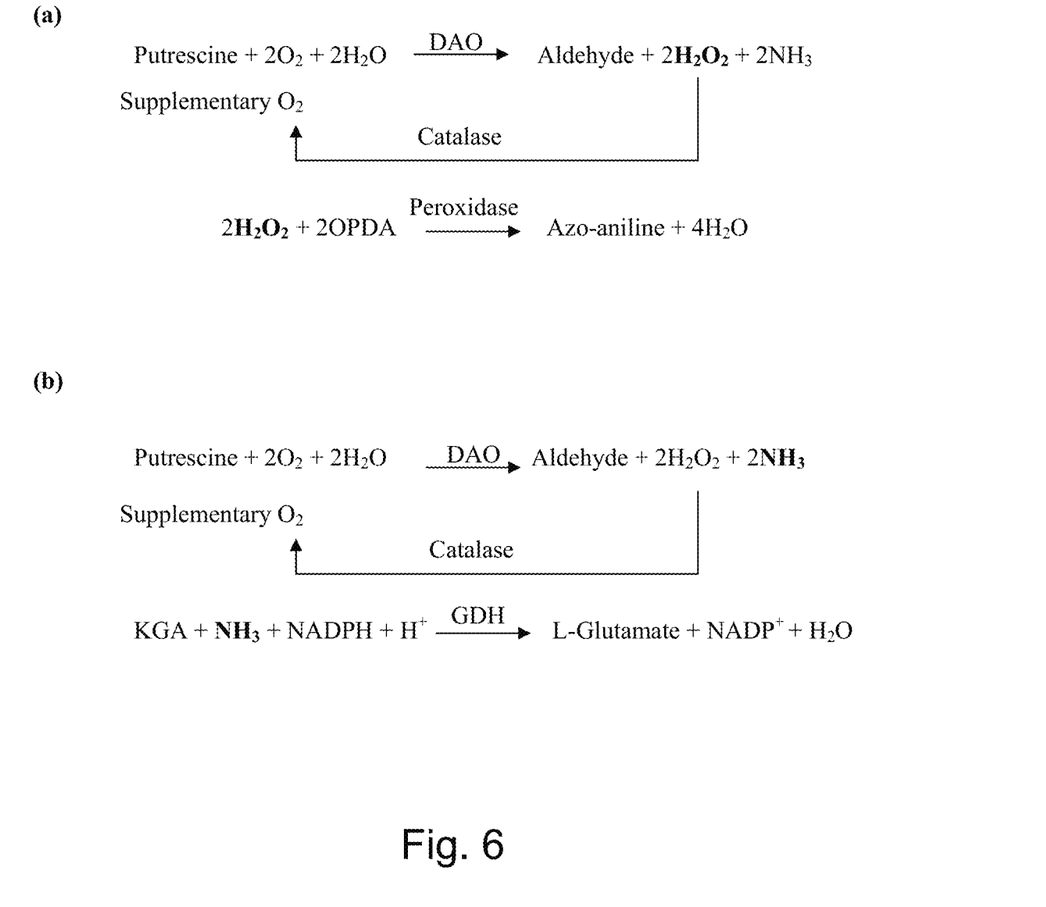
FIG. 6 illustrates schematically the enzymatic coupled reactions of DAO. Catalase decomposes $H_2O_2$ by-product of DAC, and enhances the available oxygen. This may contribute to a shift of equilibrium of DAO reaction.

To test the capacity of the bi-enzymatic system of the present invention to produce and to decompose $H_2O_2$, the two enzymatic assays for DAO enzymatic activity (detecting $H_2O_2$ and $NH_3$) of CMS:Chitosan formulations with 2:1 VDAO:Catalase or 1:1 VDAO:Catalase ratio were used (FIG. 6). Ratios of VDAO:Catalase ranging from about 9:1 to 1:9 would also be suitable. The apparent decrease of the measured DAO enzymatic activity observed for the bi-enzymatic CMS:Chitosan formulations when determined via $H_2O_2$ and peroxydase assay, is due to the decomposition of $H_2O_2$ by catalase, which is liberated from the tablets almost in the same time with DAO. When the bi-enzymatic formulation is administrated in vivo, the released DAO may degrade the histamine (endogenous from intestinal inflammatory reactions or exogenous from food) and produce $H_2O_2$, a pro-oxidant with damaging effects. Therefore, the catalase may be beneficial, particularly when liberated almost in the same time as DAO, to decompose the $H_2O_2$ from histamine catabolism or from other inflammatory reactions.

According to another embodiment of the present invention, vegetal DAO enzyme presents a high specificity for primary diamines and histamine, catalyzing their oxidation to corresponding aldehyde, $H_2O_2$ and $NH_3$. When catalase is also present (different ratios of VDAO:Catalase may be used), part of $H_2O_2$ produced by DAO is decomposed by catalase generating, thus, some supplementary $O_2$, which is expected to enhance the rate of substrate (histamine, putrescine) oxidation and to shift the equilibrium in favor of the reaction products. Thus, the action of the two enzymes can be considered as complementary. From the apparent decrease of measured DAO enzymatic activity in the presence of catalase, it is possible to determine the number of μmoles of $H_2O_2$ decomposed by catalase. The association of catalase to DAO may be therapeutically beneficial in IBD treatment, since the available fluid in the colon is reduced and the $O_2$ availability is scarce. Thus, it is believed that additional $O_2$ may be efficient for DAO activity.

Without wishing to be bound by theory, a possible role of antioxidants in therapy of IBD hypothesizes that the efficiency of current treatments in IBD can also be related to their antioxidant properties. Thus, 5-aminosalicylate reduces mucosal oxidative species production by inflamed human colorectal biopsy (Simmonds et al., *Gastroenterology* 1992; 103: 186-196) and lipid peroxidation (Ahnfelt-Ronne et al., *Gastroenterology* 1990; 98: 1162-1169). A combination of superoxide dismutase and desferrioxamine may be effective in the treatment of Crohn's disease (Emerit et al., *Free Radic Res. Commun* 1991; 12: 563-569). An antioxidant effect of catalase on colonic biopsy specimens from a rat model of colitis was also described (Millar et al., *Gut* 1996; 39: 407-415). Therefore, it is believed that the oral administration of catalase may present a therapeutic interest.

Both histaminase and catalase present a high therapeutic potential in treatment of intestinal ischemia, inflammatory diseases such as Crohn's disease, Ulcerative colitis or colonic cancer.

According to another embodiment, the catalase, when compressed as excipient-free tablet (100% catalase loading), presents gastric stability (63% remaining activity inside the tablet) due to possible intra- and inter-chains protein associations, generating an outer protective gel layer, thus preventing the gastric fluid access into the tablet and keeping dry the core of the tablets. However, the free catalase (in solution, unformulated) is almost totally degraded in the same conditions showing the essential role of the formulation. The ratio between catalase and polymeric excipients (CMS and Chitosan) may be optimized to better protect and delay the catalase delivery over 480 min in SIF, for both mono-enzymatic or bi-enzymatic VDAO:Catalase formulations. According to another embodiment of the present invention, the CMS:Chitosan formulation containing 2:1 VDAO:Catalase liberates more catalase than the bi-enzymatic formulation containing 1:1 VDAO:Catalase. It is believed that the protein-protein interactions are probably more representative at higher ratio of catalase. Although the starch used in the formulation is modified (CMS), it may remain a potential substrate, for alpha-amylase present in pancreatin, and may contribute to the release of therapeutic enzyme, which is an important advantage of CMS.

Thus, the combination of VDAO and catalase, both formulated as monolithic tablets with CMS and Chitosan co-excipients, may improve the treatment of inflammatory enteric diseases (or inflammatory bowel diseases) by reducing local inflammation through acceleration of histamine catabolism and by counteracting free radical-mediated tissue injury. These inflammatory bowel diseases include, without limitations, Crohn's disease, ulcerative colitis, collagenous colitis, lymphocytic colitis, ischemic colitis, diversion colitis, Behçet's disease, indeterminate colitis, or combination thereof.

According to another embodiment, another possible therapeutic effect of DAO may also be in allergy (e.g. such as a food allergy) or pseudo-allergic diseases by the elimination of histamine excess in intestine. Pseudo-allergies are nonimmunologic, anaphylaxis-like reaction of sudden onset, associated with food ingestion. They may be due to an anaphylactoid reaction, intolerance (e.g. psychogenic responses), metabolic defect (e.g. enzymatic deficiency), tyramine reaction, or toxicity (e.g. tetrodotoxin).

According to another embodiment, another possible therapeutic avenue may be for the treatment of cancer and intestinal tumors, such as colon and/or colorectal cancer, due to the anti-neoplastic properties of amine oxidases (Toninello et al., *Biochim Biophys Acta* 2006; 1765: 1-13).

According to another embodiment, a possible therapeutic avenue may be for the treatment of histamine intolerance (histaminose) which results from a disequilibrium of accumulated histamine and the capacity for histamine degradation. Histamine intolerance refers to a reaction to foods that have high levels of naturally occurring histamine; in contrast, during a normal allergic reaction, the body itself produces high levels of histamine in response to a food allergen it perceives as an invader. People with histamine intolerance often have low levels of either of two enzymes, diamine oxidase (DAO) and histamine-N-methyltransferase (HNMT) that bind to and metabolize histamine. In these people, histamine can build up over time and cause symptoms throughout the body. The most common symptoms of histamine intolerance are migraine headaches, gastrointestinal symptoms (such as diarrhea), flushing, hives, eczema, and allergic rhinitis. Histamine intolerance can also cause more severe symptoms. It can trigger asthma attacks or anaphylactic shock, can cause arrythmia, and may be associated with serious chronic conditions like Crohn's disease.

The anti-inflammatory activity of VDAO associated to catalase (having the capacity of clearing the pro-oxidant hydrogen peroxide) represents a new concept for treatment of intestinal dysfunctions.

When orally administered, the enzymes for intestinal targeting are susceptible to degradation during gastric and intestinal transit. In the stomach, the enzymes can be affected by acidic and pepsinolytic degradation, whereas in upper intestine, pancreatic and intestinal proteases also generate massive degradation of the enzymes. Thus, there is a need to formulate the enzymes with excipients affording both gastric and intestinal protection.

Generally, currently proposed systems useful for colonic delivery are based either i) on pro-drugs where the release of the active form is based on the capacity of the enzymes produced by the colonic flora to act on polysaccharides or ii) on functional coatings surrounding monolithic matrices and ensuring dosage form transportation to the site of action. However, these systems are not concerned with the colonic delivery of therapeutic enzymes via an oral dosage form obtained by direct compression without functional coatings. The system of the present invention is a different system comprising coating-free monolithic tablets obtained by direct compression of dry powders of CMS and Chitosan excipients mixed with freeze-dried proteins (e.g. enzymes).

Our proposed formulations represent an innovative and non-toxic bi-functional enzyme therapeutic approach for intestinal diseases and provide a solution of unmet needs.

Oral dosage forms can be obtained by direct compression of active dry powders mixed with selected excipients: i.e. cellulose derivatives, metacrylates, chitosan, carboxymethylstarch (CMS), or their mixtures. They can be administrated as tablets, capsules containing multiparticulates and/or powders.

According to another embodiment of the present invention, the proposed dosages can be formulated with pharmaceutical excipients with or without pH-dependency. For selected excipients, the oral dosages exhibit protective effects depending on gel-like structure formed after their exposure to simulated gastric fluid.

The proteins loading play also a role being correlated with the self-assembling phenomena.

Chitosan, a polysaccharide consisting of β-(1,4)-linked 2-amino-2-deoxy-D-glucose still presenting a certain number of 2-acetamido-2-deoxy-D-glucose units, is insoluble at the pH of the intestinal fluids. It may be an interesting excipient for site-specific delivery to the colon due to its susceptibility to glycosidic hydrolysis by microbial enzymes in the colon.

Other suitable cationic polymers include without limitations, derivatives of chitosan, such as aminoethylchitosan, and tri-methylaminochitosan, polylysine, or an aminoethyl methacrylic copolymer, or combinations thereof. For example, cationic methacrylate copolymers carrying dimethyl aminoethyl functional groups type include without limitations EUDRAGIT® E PO (powder). The preferred cationic polymer is chitosan.

The association of cationic chitosan with other biodegradable polymers, such as anionic polymers including without limitations carboxymethylcellulose, carboxymethylstarch (CMS), alginates, pectins, a methacrylic copolymer carrying carboxylic groups, an hydroxypropylmethylcellulose phthalate, an hydroxypropylmethylcellulose acetate succinate, and combinations thereof may be an interesting way to deliver bioactive agents to the colon. The preferred anionic polymer is carboxymethylstarch (CMS). Anionic methacrylic copolymers carrying carboxylic functional groups type include for example EUDRAGIT® L 100/S 100/L 100-55 (powders).

According to another embodiment, the association of cationic polymers and/or anionic polymers with other biodegradable polymers, may also include polymers chosen from pH-independent materials (i.e. neutral polymers) such as neutral cellulose ethers (methocel and ethocel grades), poly(ethylene oxide)—ex Polyox various grades or methacrylate copolymers neutral esters (Eudragit RL/RS PO). According to an embodiment, the neutral polymer may comprise a polyhydroxylic polymer. Non-limiting examples of such polyhydroxyk polymer include hydroxypropylmethylcellulose, ethylcellulose, polyethylene oxide, a methacrylate copolymer neutral ester, a cellulose ether, or combinations thereof.

Methacrylate copolymers neutral esters, such as EUDRAGIT® RL or RURS, are pH-independent and ensure an intestinal delivery by controlling drug release via their permeability.

Methocel® are non-ionic derivatives used as matrices for controlled release. The matrix forming grades METHOCEL® include for example grades E50LV, K100LV, K100LV CR K4M, K15M, K100M, E4M, E10M, K4MCR, K15MCR, K100MCR, E4MCR, E10MCR, which exhibit a fast hydration and gel-forming properties.

Polyox, or Polyethylene oxide are matrix forming polymers which are nonionic, high molecular weight water-soluble poly (ethylene oxide) polymers. Molecular weights range from 100,000 to about 8,000,000. They exhibit many properties that are typical of other classes of water-soluble polymers—lubricity, binding, water retention, thickening, and film formation. Suitable grades include but are not limited to WSR N-10, N-80, N-205, N-750, N-3000, N-303, N-308.

In accordance with another embodiment, the tablet of the present invention may be coated or uncoated. According to an embodiment, the coating may comprise, for example, compounds such as hydroxypropylmethylcellulose phthalate, hydroxypropylmethylcellulose acetate succinate, ethylcellulose, and a polymethacrylate derivative such as methacrylate copolymers with carboxylic groups (series of Eudragit L and S), such as Eudragit L 30 D-55/FS 30 D (aqueous dispersions 30%), Eudragit L 12.5/S 12.5 (organic solution 12.5%). Hydroxypropylmethylcellulose phthalate is an enteric film coating material or a matrix binder used in solid dosage forms. It is used as a viscosity control agent, gelling agent, film former, stabilizer, dispersant, lubricant, binder, emulsifying agents, and suspending agent. Hydroxypropylmethylcellulose acetate succinate is an enteric film coating material. Ethylcellulose is a matrix and film forming polymer. Eudragit NE 30 D, RURS 12.5 are also pH-independent film forming polymers.

In accordance with another embodiment, the tablet of the present invention may also comprise any of suitable bioactive agents. According to another embodiment of the present invention, the bioactive agent may be at least one of a protein, a drug, a pro-drug (e.g. such as prednisone), and an anti-oxidant (e.g. vitamin C and E, carotenoids, such as beta-carotene), a bacteria (e.g. such as *Lactobacillus* sp., *Bifidobacterium* sp.), or combinations thereof. The protein may be any suitable proteins. The proteins may be other enzymes. According to an embodiment, the total amount of enzyme may be from about 3.3% to about 10%, or from about 3.3% to about 20%, or from about 3.3% to about 30%, or from about 3.3% to about 40%, or from about 3.3% to about 50%, or from about 3.3% to about 60%, or from about 3.3% to about 70%, or from about 3.3% to about 80%, or from about 3.3% to about 90%.

Bioactive agents of interest include any suitable drugs, which include without limitations, non-steroidal anti-inflammatory drugs (NSAID) chosen from ibuprofen, naproxen, benoxaprofen, flurbiprofen, fenoprofen, fenbufen, ketoprofen, loxoprofen, pranoprofen, carprofen, oxoprofen, microprofen, tioxaprofen, suprofen, alminoprofen, fluprofen, aspirin, diflunisal, salsalate, olsalazine, sulfasalazine, mesalamine, indomethacin, sulindac, etodolac, ketorolac, diclofenac, mefenamic acid, meclofenamic acid, flufenamic acid, tolfenamic acid, celecoxib, valdecoxib, rofecoxib, etoricoxib or the combination thereof.

Drugs also include histamine antagonist (antihistamine), such as $H_1$-receptor antagonists chosen from Cetirizine, Chlorpheniramine, Clemastine, Desloratadine, Dexchlorpheniramine, Dimenhydrinate, Dimetindene, Diphenhydramine, Doxylamine, Ebastine, Embramine, Fexofenadine, Levocetirizine, Loratadine, Meclozine, Olopatadine, Pheniramine, Promethazine, Quetiapine, or combinations thereof, and/or $H_2$-receptor antagonist is chosen from Cimetidine, Famotidine, Lafutidine, Nizatidine, Ranitidine, Roxatidine.

According to another embodiment, there is disclosed an intestinal delivery composition for treating or alleviating intestinal inflammation, which includes a therapeutically effective amount of a histaminase enzyme and a catalase enzyme, in association with an acceptable intestinal delivery pharmaceutical formulation comprising at least one excipient as a matrix former. Preferably, the composition is an oral dosage form.

According to an embodiment, the histaminase is a vegetal histaminase, such as *Pisum sativum* L. histaminase, *Lens culinaris* histaminase, *Cicer arietinum* histaminase, *Lathyrus sativus* histaminase, and mixtures thereof. Preferably, the vegetal histaminase is pea seedlings DAO.

According to another embodiment, the ratio of histaminase enzyme and catalase enzyme present in the composition may be from about 9:1 to about 1:9. Preferably, the ratio is from about 1:1 to about 2:1.

According to an embodiment, the excipient may include a cationic polymer, or an anionic polymer, or a combination of a cationic polymer and an anionic polymer. Non limiting examples of anionic polymers include carboxymethylcellulose, carboxymethylstarch, an alginate, a pectin, a dextran sulfate, a methacrylic copolymer carrying carboxylic groups, an hydroxypropylmethylcellulose phthalate, an hydroxypropylmethylcellulose acetate succinate, or combinations thereof. Anionic methacrylic copolymers carrying carboxylic functional group type include for example EUDRAGIT® L 100/S 100/L 100-55 (powders) with gastro-resistant properties.

Non limiting examples of cationic polymers include a chitosan, a derivative of chitosan, a polylysine, or an aminoethyl methacrylic copolymer, or combinations thereof. For example, cationic methacrylate copolymers carrying dimethyl aminoethyl functional groups type include without limitations EUDRAGIT® E PO (powder).

According to an embodiment of the present invention, the ratio of the cationic polymer and anionic polymer are present in the composition may be from about 1:9 to about 9:1, and preferably the ratio is 1:1.

According to another embodiment, the association of cationic polymers and/or anionic polymers with other biodegradable polymers, may also include polymers chosen from pH-independent materials (i.e. neutral polymers) such as neutral cellulose ethers (methocel and ethocel grades), poly(ethylene oxide)—ex Polyox various grades or methacrylate copolymers neutral esters (Eudragit RL/RS). According to an embodiment, the neutral polymer may comprise a polyhydroxylic polymer. Non-limiting examples of such polyhydroxylic polymer include hydroxypropylmethylcellulose, ethylcellulose, polyethylene oxide, a methacrylate copolymer neutral ester, a cellulose ether, or combinations thereof.

Methacrylate copolymers neutral esters, such as EUDRAGIT® RL or RL/RS, are pH-independent and ensure an intestinal delivery by controlling drug release via their permeability.

Methocel® are non-ionic derivatives used as matrices for controlled release. The matrix forming grades METHO- CEL® include for example grades E50LV, K100LV, K100LV CR K4M, K15M, K100M, E4M, E10M, K4MCR, K15MCR, K100MCR, E4MCR, E10MCR, which exhibit a fast hydration and gel-forming properties.

Polyox, or Polyethylene oxide, are matrix forming polymers which are nonionic, high molecular weight water-soluble poly (ethylene oxide) polymers. Molecular weights range from 100,000 to about 8,000,000. They exhibit many properties that are typical of other classes of water-soluble polymers—lubricity, binding, water retention, thickening, and film formation. Suitable grades include but are not limited to WSR N-10, N-80, N-205, N-750, N-3000, N-303, N-308.

According to an embodiment, the intestinal delivery composition of the present invention may further comprise a coating, which may comprise, for example compounds such as hydroxypropylmethylcellulose phthalate, hydroxypropylmethylcellulose acetate succinate, ethylcellulose, and a polymethacrylate derivative such as methacrylate copolymers with carboxylic groups (series of Eudragit L and S). Hydroxypropylmethylcellulose phthalate is an enteric film coating material or a matrix binder used in solid dosage forms. It is used as a viscosity control agent, gelling agent, film former, stabilizer, dispersant, lubricant, binder, emulsifying agents, and suspending agent. Hydroxypropylmethylcellulose acetate succinate is an enteric film coating material. Ethylcellulose is a matrix and film forming polymer that is pH-independent. Eudragit NE 30 D, RURS 12.5 are also pH-independent film forming polymers.

According to another embodiment, there is disclosed a method of treating intestinal inflammation comprising administering a therapeutically effective amount of a composition according to the present invention.

The present invention will be more readily understood by referring to the following examples which are given to illustrate the invention rather than to limit its scope.

Example 1

Preparation of Diamine Oxidase Vegetal Extract from Seedlings of *Lathyrus Sativus* (Grass Pea)

A vegetal preparation from grass pea seedlings (VDAO) is obtained from 500 g of freshly collected shoots of etiolated *L. sativus* seedlings which are homogenized in a Waring blender with 1 L of 30 mM $NaH_2PO_4$ (final pH 4.4) and then filtered. The solid residue is mainly constituted by cell walls and vascular fibres, and was washed with the same buffer. The enzyme was finally eluted from the solid residue with 0.1M sodium phosphate buffer and then centrifuged. The supernatant containing the DAO was lyophilized, obtaining the DAO vegetal extract powder, hereto called VDAO.

Example 2

Proposed Excipients

Synthesis of Carboxymethylstarch

The CMS excipient was synthesized by starch treatment with monochloroacetic acid in an alkaline medium, as previously described (Calinescu et al., *Int J Pharm* 2007; 343: 18-25). Practically, an amount of 70 g high amylose starch (Hylon VII) was suspended in 170 mL of distilled water and warmed at 50° C. under continuous stirring in a Hobart™ planetary mixer. A volume of 235 mL of an aqueous 1.45 M NaOH solution was added and the reaction medium was homogenized for 20 min at 50° C. for gelatinization. To transform the starch into a more reactive alkoxide form (and thus favorising the starch nucleophilic substitution), 55 mL of 10 M NaOH solution were also added to the rectional medium. Then, 45.5 g of monochloroacetic acid, dissolved in, a minimum volume of water, were added to the starch and the reaction medium was kept for 1 h at 50° C. for the reaction of substitution. After 1 h of reaction (50° C.), the gel-slurry was neutralized with an acetic acid solution and precipitated with acetone, and the salts ions were removed by several washings with acetone/water (60:40, v/v). Finally, the CMS gel-slurry is dried with acetone and kept overnight at room temperature.

Preparation of Chitosan Excipient

The powder of Chitosan was prepared as previously described (Calinescu and Mateescu, *Eur J Pharm Biopharm* 2008; 70: 582-589), by dissolving the Chitosan in an acetic acid solution (2%), followed by its filtration and treatment with NaOH (1M) until a pH of 6.5. The gel-slurry was precipitated with 100% acetone, well-washed with distilled water, and finally dried at room temperature.

The polymer powders were sieved and particles with granulometry less than 300 μm are retained for the preparation of monolithic tablets.

Example 3

Vegetal Diamine Oxidase Monolithic Tablets

The powders of CMS and/or Chitosan excipients were well mixed with the bioactive agents until homogenization. Tablets (300 mg), obtained by direct compression (2.5 T) of the powder mixtures using a 9 mm cylinder outfits and a Carver press (Wabash, 1N, USA), are formulated with VDAO powder (30% loading), as active principle ingredient (API), and CMS alone, CMS:Chitosan (1:1, w/w) or Chitosan alone, as excipients.

Example 4

Catalase Monolithic Tablets

The powders of CMS and/or Chitosan excipients were well mixed with the bioactive agents until homogenization. Catalase tablets of 300 mg were also obtained by direct compression (2.5 T) of the powder mixtures using a 9 mm cylinder outfits and a Carver press (Wabash, 1N, USA). Various enzyme loading from 3.3%, 10%, 20%, to 50% were obtained using CMS:Chitosan (1:1, w/w).

Example 5

Bi-Enzymatic Monolithic Tablets

The powders of CMS and/or Chitosan excipients were well mixed with the bioactive agents until homogenization. Tablets of 300 mg and 9 mm diameter, based on CMS:Chitosan (1:1, MO and containing VDAO or variable ratios of VDAO:Catalase (i.e., 1:1 and 2:1), are also obtained at 2.5 T.

Example 6

Behavior of Monolithic Tablets 1N Simulated Gastric Fluid

Figure 1:
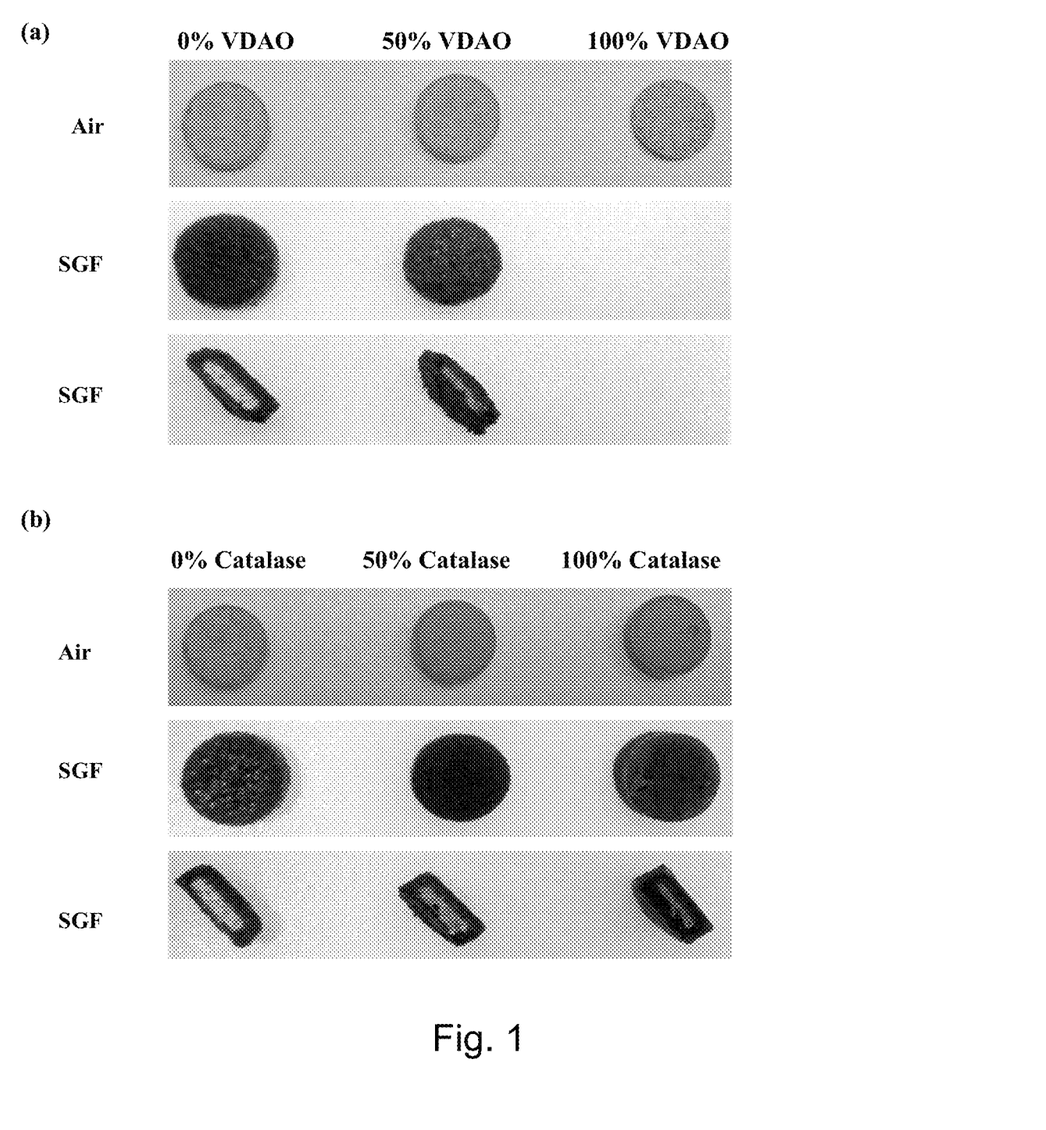
FIG. 1 illustrates pH, stability of enzyme formulations based on Carboxymethylstarch:Chitosan (CMS:Chitosan). Monolithic tablets based on CMS:Chitosan (1:1) with 0% and 50% (a) diamine oxidase vegetal extract (VDAO) or (b) catalase, containing bromocresol green (pH indicator). Untreated (air) or incubated tablets for 60 min in simulated gastric fluid containing pepsin, at 50 rpm and 37° C. (whole and cross-sections of tablets). The blue color indicates protection against gastric acidity.

This is an example of the present invention regarding the behavior of monolithic tablets in simulated gastric fluid (SGF). Tablets of 300 mg, based on CMS:Chitosan (1:1) with 0% and 50% enzyme loading and on 100% enzyme, all containing 5% bromocresol green (15 mg pH indicator per tablet), are prepared as previously described in examples 3 and 4. Every tablet is incubated 60 min in 50 mL of SGF (pH 1.2) at 37° C. and 50 rpm (incubator shaker—series 25D, New Brunswick Scientific Co., NJ, USA). The tablet integrity and color modifications are noticed on their whole shapes and on cross-sectioned tablets (FIGS. 1a, b).

This test is indicating to which extent the proposed excipients can prevent the penetration of acidic fluid into the tablet by following the color change of the pH indicator from blue (over pH 5.4) to yellow-orange (below pH 3.8). Prior to incubation in SGF, the dry tablets based on CMS:Chitosan (1:1) unloaded (0%) and loaded with 50% VDAO or with catalase, presented some blue points at the external surface, coming from the pH indicator (FIGS. 1a, b). The surface of the entire tablets based on CMS:Chitosan excipients (with 0% and 50% enzyme loading) is blue during the 60 min of acidic incubation (SGF), showing a protection afforded by the formulation. At the surface of the whole tablets, some small orange regions are also detected, corresponding to a presence of acidity (mostly limited at the very outer layer). When the tablets are cross-sectioned, the core of the tablets is dry, with no gastric fluid inside the tablets and, consequently, no solubilization of the bromocresol green particles. Furthermore, a peripheral blue layer (pH greater than 5.4) close to the surface of the tablets is found (FIGS. 1a, b) indicating that the tablets form a gel barrier at the surface, affording thus a protection against gastric acidity, despite the fact that the tablets are not coated with gastro-protective materials. The presence of high loading of catalase in the formulations may also contribute to gastro-protection of the proposed tablets.

Example 7

Stability of Histaminase Formulations in Simulated Gastric Fluid

Figure 2:
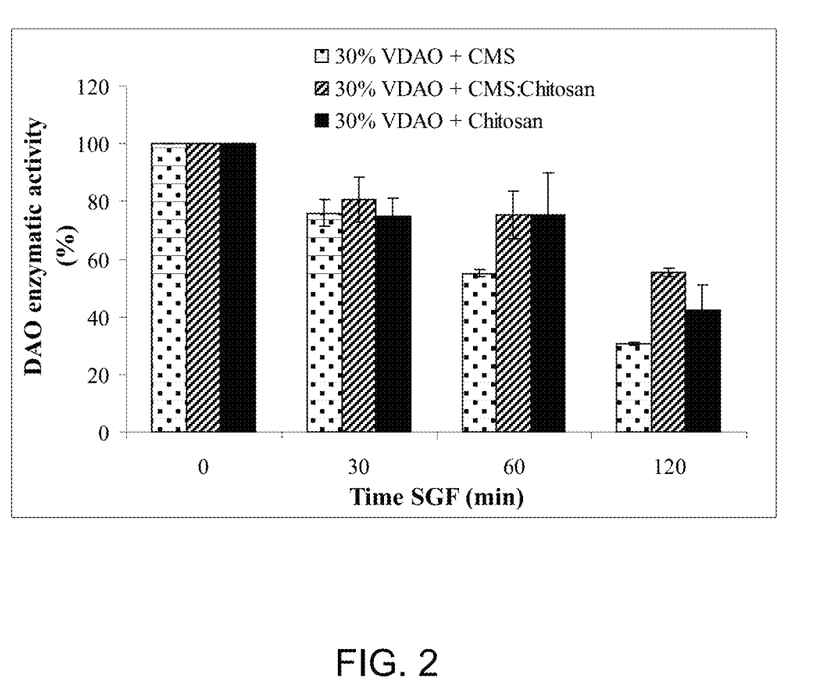
FIG. 2 illustrates in vitro gastric stability of vegetal DAO (VDAO) in different formulations. Monolithic tablets based on CMS, CMS:Chitosan (1:1) or Chitosan and containing 30% VDAO were incubated up to 120 min in simulated gastric fluid (SGF with pepsin). DAO remaining enzymatic activity (%) inside the tablets was determined after different periods of SGF treatment. The DAO activity is expressed in percentages, considering as 100% the values determined in 50 mL phosphate buffer at 0 min: for DAO formulated with CMS, the 100% was 0.45±0.032 EU/mL original sample, for CMS:Chitosan 0.41±0.019 EU/mL original sample, and for Chitosan 0.40±0.03 EU/mL original sample (n=3).

Tablets based on CMS alone, CMS:Chitosan (1:1) or Chitosan alone, containing 30% VDAO, are incubated for 0, 30, 60, 120 min in 50 mL simulated gastric fluid (SGF) with pepsin (USP, 2000), at 37° C. and 50 rpm. The remaining enzymatic activities are determined on crushed tablets after incubation times indicated above in a 50 mL potassium phosphate buffer (50 mM, pH 7.0). Formulations based on CMS, CMS:Chitosan (1:1) or Chitosan and containing 30% VDAO presented a certain stability in SGF conditions (pH 1.2, pepsin) during all the periods of incubation. After 60 min of gastric treatment, CMS:Chitosan (1:1) and Chitosan formulations ensured a similar protection of VDAO keeping 75% activity (FIG. 2). Finally, after 120 min of incubation, the CMS:Chitosan matrix presented a better efficacy in term of protection of VDAO, with a 55.5% remaining VDAO activity found inside the tablet.

Example 8

Histaminase Delivery in Simulated Intestinal Fluid

Figure 3:
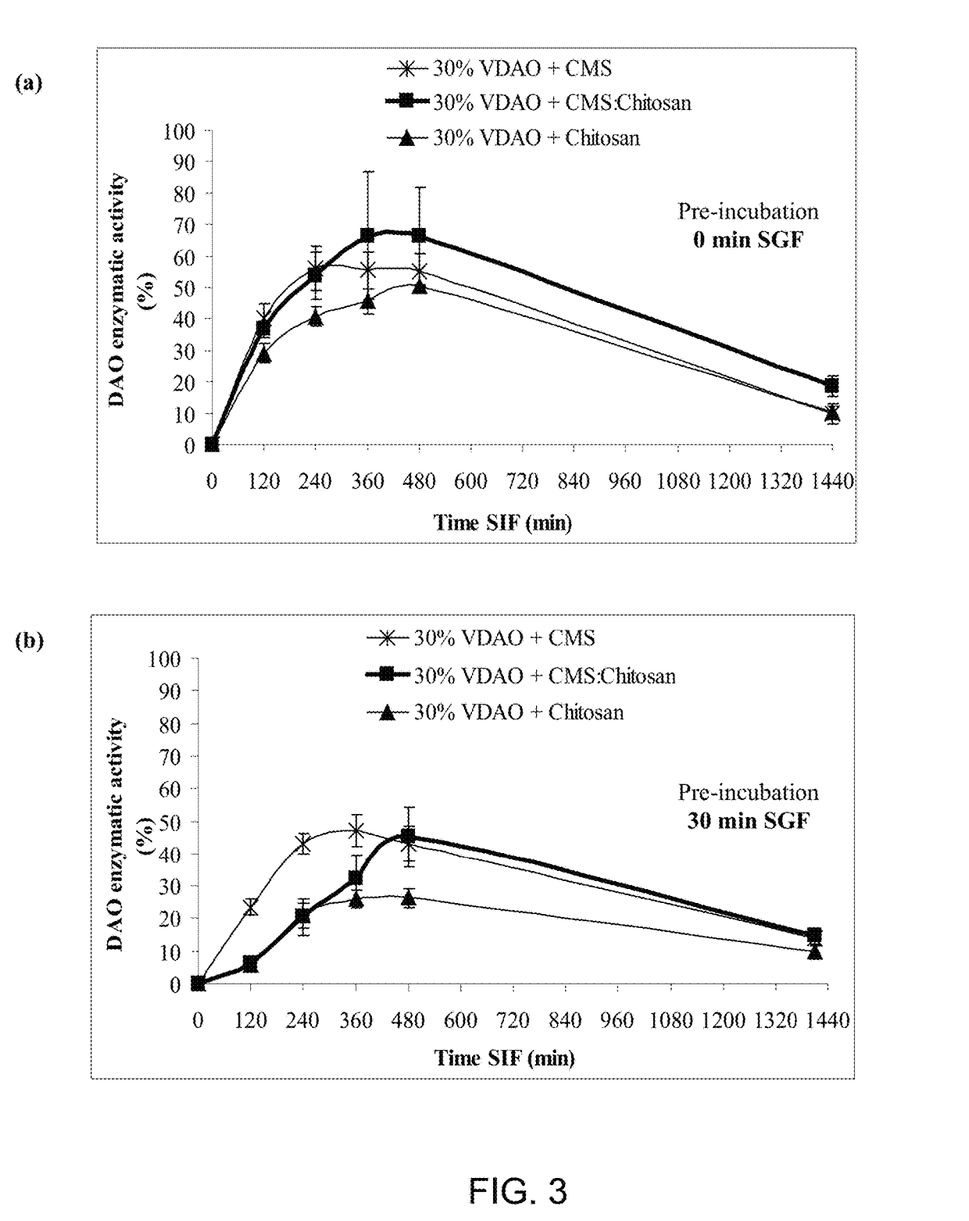
FIG. 3 illustrates in vitro intestinal delivery of vegetal DAO (VDAO) from different formulations. Monolithic tablets based on CMS, CMS:Chitosan (1:1) or Chitosan and containing 30% VDAO were incubated up to 120 min in simulated gastric fluid (SGF with pepsin). The liberation of DAO (%) from monolithic tablets in simulated intestinal fluid (SIF with pancreatin) after 0 min (a), 30 min (b), 60 min (c) and 120 min (d) in SGF incubation (50 rpm and 37° C.). The DAO activity is expressed in percentages, considering as 100% the values determined in 50 mL phosphate buffer at 0 min: for DAO formulated with CMS, the 100% was 0.45±0.032 EU/mL original sample, for CMS:Chitosan 0.41±0.019 EU/mL original sample, and for Chitosan 0.40±0.03 EU/mL original sample (n=3).

VDAO tablets are also incubated in simulated intestinal fluid (SIF) only, without previous incubation in SGF. Thus, when incubated directly in SIF, the absence of the external gel of Chitosan generates a faster liberation of VDAO for CMS:Chitosan and Chitosan formulations (FIG. 3a) in comparison with the same formulations previously incubated in SGF (30, 60, 120 min), where the outer gel delayed the VDAO delivery (FIGS. 3b-d). The longer release from chitosan alone may be related to a rearrangement of chitosan in acidic media (Leonida and Mateescu, Transactions of the 33$^{rd}$ Annual Meeting of the Controlled Release Society, 2006). The formulation based on CMS:Chitosan (1:1) presents a better delivery of VDAO than the Chitosan formulation (FIG. 3a-d), probably due to the fact that the release time can also be modulated by alpha-amylase from pancreatin, acting on CMS excipient and thus accelerating the VDAO delivery. Tablets based on CMS alone, are not suitable for colon delivery because of their fast dissolution in SIF medium containing pancreatin.

Example 9

Catalase Monolithic Tablets Behaviour in SGF and SIF

Figure 4:
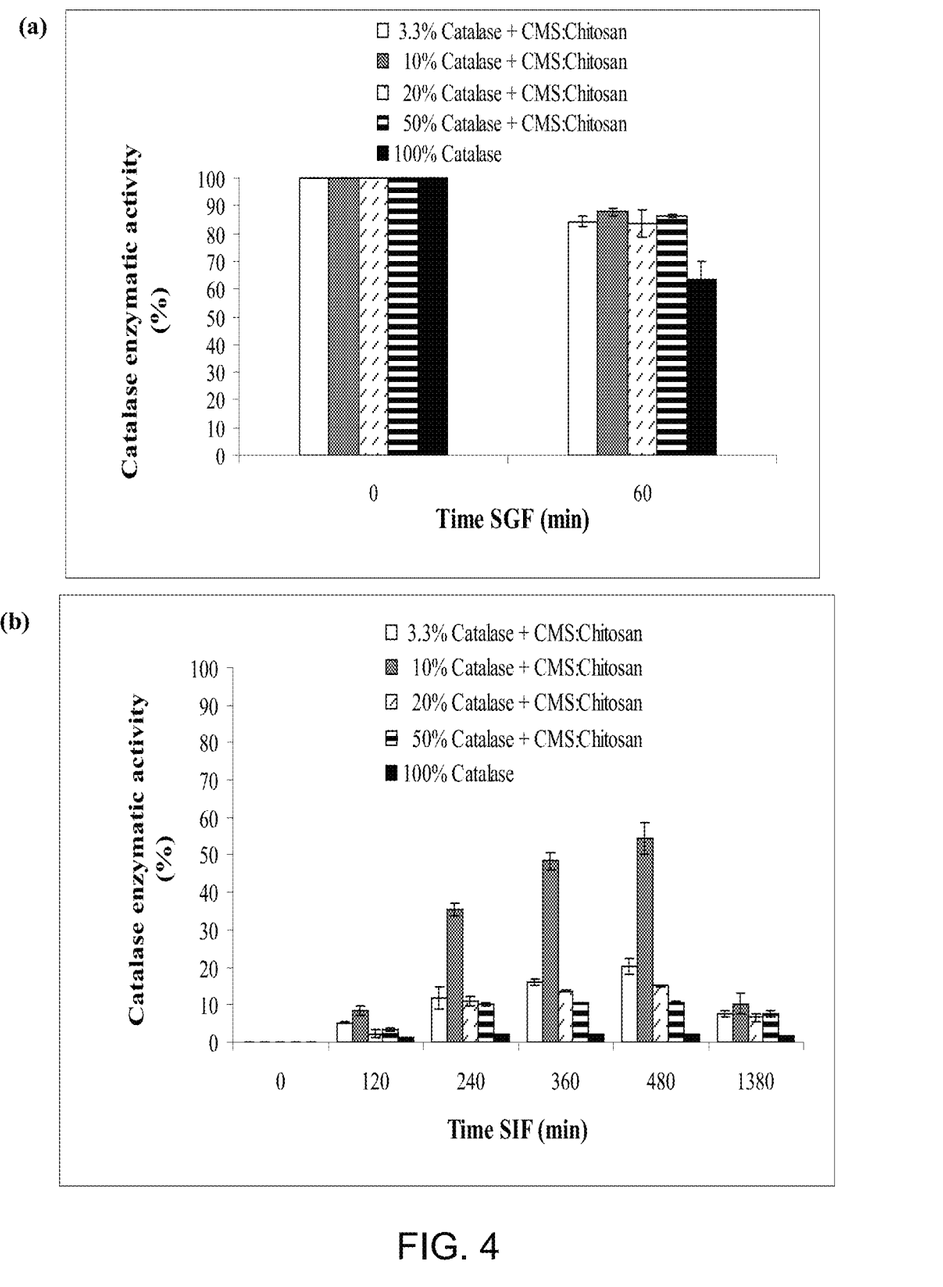
FIG. 4 illustrates gastric stability and intestinal release of different loadings of catalase formulated with CMS:Chitosan. Monolithic tablets of CMS:Chitosan (1:1) with increasing loading of catalase and of 100% catalase (excipient-free) were incubated for 60 min in simulated gastric fluid (SGF with pepsin) at 50 rpm and 37° C. The enzymatic activity of catalase (%) was evaluated after 60 min of gastric incubation of tablets (a) and during the liberation in simulated intestinal fluid (containing pancreatin), after a previous SGF treatment of 60 min (b). Catalase enzymatic activity is expressed in percentages, considering for each loading, as 100%, the catalase activity formulated with CMS:Chitosan, determined in 50 mL phosphate buffer at 0 min (n=3).

Catalase, is formulated with CMS:Chitosan (1:1) at different loadings as described in Example 4. At increasing catalase loading from 3.3% to 50%, its residual enzymatic activity found inside the tablet remains relatively constant (more than 80%) after 60 min of SGF incubation, suggesting that the catalase can undergo a kind of self-protection by possible protein-protein interactions in addition to the relative protection afforded by the excipients (FIG. 4a). The formulation of 100% catalase tablets (excipient-free) presented a relatively good stability in gastric medium (60 min), with 63% catalase remaining enzymatic activity per tablet (FIG. 4a). However, the presence of polymeric excipients is beneficial (more than 80% residual activity). Higher loading in catalase per tablet did not deliver higher percentages of catalase in SIF medium (FIG. 4b). Only the CMS:Chitosan formulation containing 10% catalase released more than 50% catalase (enzymatic activity) after 480 min of SIF incubation. Protein-protein assembling in the case of catalase can explain lesser release at increasing loading.

Example 10

Bi-Enzymatic Monolithic Tablets

Figure 5:
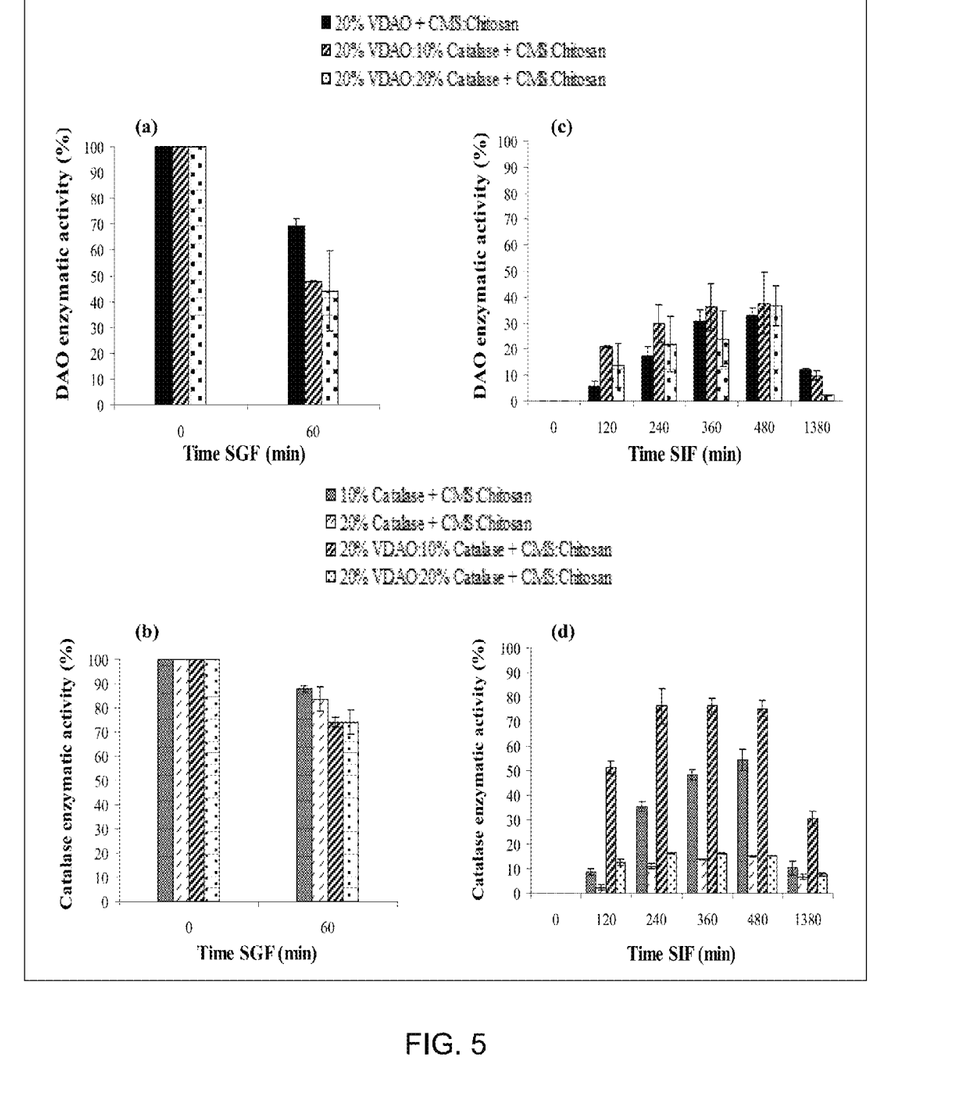
FIG. 5 illustrates mono- and bi-enzymatic CMS:Chitosan formulations containing DAO vegetal extract (VDAO) and/or catalase. Gastric stability in simulated gastric fluid containing pepsin (0 and 60 min) of (a) VDAO and (b) catalase as mono- and bi-enzymatic formulations based on CMS:Chitosan (1:1) and their liberation in simulated intestinal fluid containing pancreatin (c, d), after 60 min incubation of tablets in gastric medium. The enzymatic activity of DAO (20% loading: 0.39±0.0011 EU/mL original sample) and of catalase (10% and 20% loading), formulated as mono- and bi-enzymatic CMS:Chitosan tablets, and determined in 50 mL phosphate buffer (0 min), was considered as 100% (n=3).

The tablet formulations containing the two enzymes are incubated in SGF in the same incubation conditions as indicated above. After incubation, tablets are individually transferred into 50 mL SIF, pH 6.8, with pancreatin (USP, 2000) and incubated at 37° C. and 50 rpm (total dissolution time of 24 h). A volume of 1 mL is sampled from SIF after regular intervals of time, filtered and the DAO and catalase enzymatic activities are determined. The presence of catalase in the VDAO formulation diminishes the determined DAO remaining enzymatic activity inside the tablet after 60 min of SGF incubation, either for 10% or 20% catalase (FIG. 5a). A reduction of remaining catalase activity, after 60 min in SGF, is also observed for the formulations containing the VDAO (FIG. 5b). For the bi-enzymatic formulations with CMS:Chitosan, the presence of 10% or 20% catalase does not significantly modify the DAO liberation (FIG. 5c). Differently, for the same formulations, the presence of 20% VDAO preparation increases the catalase liberated in SIF medium (FIG. 5d) due to the presence of phosphate salts in VDAO powder. This increase is more accentuated for the formulation containing 20% VDAO:10% Catalase than in the case of the formulation containing 20% VDAO:20% Catalase.

Example 11

Determination of DAO Enzymatic Activity

Enzymatic Assay of DAO with the Peroxidase Coupled Reaction (Specific for Released $H_2O_2$).

The DAO enzymatic activity is spectrophotometrically assayed with a peroxidase coupled reaction: the rectional mixture containing 640 µL of 50 mM potassium phosphate buffer (pH 7.0), 10 µL of peroxidase solution (0.1 mg/mL), 50 µL of 30 mM OPDA solution and 200 µL of 30 mM putrescine solution is incubated for 5 min at 37° C. and then, 100 µL of DAO sample are added to start the dosage. The enzymatic reactions are conducted at 37° C. for 10 min. Then, 100 µL of HCl (4 M) are added and the final absorbance is read at 484 nm using a Beckman DU®-6 spectrophotometer. The standard curve is prepared with serial concentrations of $H_2O_2$ from 0 to 68 µM.

Enzymatic Assay of DAO with the L-Glutamate Dehydrogenase (GDH) Coupled Reaction (Specific for Released $NH_3$).

In the case of the association of DAO with catalase, the DAO assay via peroxidase cannot be applied due to decomposition of $H_2O_2$ by the associated catalase. For these cases, the DAO enzymatic activity is also evaluated using an ammonia assay kit (Sigma-Aldrich), where $NH_3$ released from the putrescine substrate (under DAO catalysis) reacts with alpha-ketoglutaric acid (KGA) and reduced nicotinamide adenine dinucleotide phosphate (NADPH) in the presence of GDH. The rectional mixture containing 1 mL of assay kit reagent (KGA and NADPH), 200 µL of 30 mM putrescine solution, 10 µL of GDH (kit reagent) is incubated for 5 min at 37° C. and, finally, 100 µL of DAO samples (containing or not catalase) were added. The enzymatic reactions are conducted at 37° C. for 10 min, monitoring the decrease of absorbency at 340 nm. Since catalase also strongly binds NADPH in its active center, the catalase interference is subtracted from each determination of DAO enzymatic activity.

One enzymatic unit (EU) of DAO is defined as the amount of enzyme catalyzing the oxidation of 1.0 µmole of putrescine per 10 min at pH 7.0 and 37° C.

For CMS, CMS:Chitosan (1:1) and Chitosan formulations containing 30% VDAO only, the DAO enzymatic activity is determined by the peroxidase coupled assay.

For the formulations based on CMS:Chitosan (1:1) and containing 20% VDAO and different loadings in catalase (0%, 10% and 20%), the DAO enzymatic activity is determined by the peroxidase coupled assay and by the GDH coupled assay.

The DAO enzymatic activity of vegetal extract powder (VDAO) and of different weight ratios of VDAO:Catalase powders, is also evaluated by the two enzymatic reactions, as proposed before.

Using the peroxidase coupled assay, an apparent decrease of DAO enzymatic activity is obtained in the presence of catalase in function of VDAO:Catalase ratios, due to the diminution of released $H_2O_2$ (substrate for catalase). Using the GDH coupled assay, the DAO enzymatic activity is found constant for the same VDAO:Catalase ratios, because the assay measures specifically $NH_3$ and not $H_2O_2$, showing that the DAO enzymatic activity is not affected by the presence of catalase.

The DAO liberation in SIF from the VDAO:Catalase bi-enzymatic CMS:Chitosan tablets, evaluated with the peroxidase coupled assay, shows an apparent reduction of released DAO measured activity more accentuated for the formulation containing a higher loading of catalase (20% VDAO:20% Catalase) compared to the mono-enzymatic formulation containing 20% VDAO only. When DAO liberation in SIF was determined by the GDH coupled assay (specific for the $NH_3$ released), no significant differences are obtained between the mono-enzymatic VDAO formulation and the bi-enzymatic formulations containing 10% or 20% catalase.

Example 12

Determination of Catalase Enzymatic Activity

The enzymatic activity of catalase is determined spectrophotometrically (Beckman DU®-6) by monitoring at 240 nm the $H_2O_2$ decrease during catalysis. The rectional medium contained: 2.9 mL of $H_2O_2$ (0.036%) prepared in 50 mM potassium phosphate buffer (pH 7.0) and 0.1 mL of filtered sample containing catalase.

One enzymatic unit (EU) of catalase is defined as the amount of enzyme decomposing 1.0 µmole of $H_2O_2$ per minute at pH 7.0 and 21° C., while the $H_2O_2$ concentration falls from 10.3 mM to 9.2 mM.

Protein concentrations of the VDAO and of catalase powders were determined by the method of Lowry using bovine serum albumin as standard.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A gastro-resistant monolithic solid dosage form for the oral administration of therapeutic enzymes with intestinal delivery comprising a mixture of:
    a cationic polymer chosen from a chitosan, polylysine, an aminoethyl methacrylic copolymer, or a combination thereof, and an anionic polymer chosen from carboxymethylcellulose, carboxymethylstarch, a pectin, a methacrylic copolymer carrying carboxylic groups, an hydroxypropylmethylcellulose phthalate, an hydroxypropylmethylcellulose acetate succinate, or a combination thereof; and
    a therapeutically effective amount of an isolated histaminase enzyme and an isolated catalase enzyme, in a ratio of about 9:1 to 1:9.

2. The oral dosage form according to claim 1, further comprising a neutral polymer.

3. The oral dosage form according to claim 2, wherein said neutral polymer comprises a polyhydroxylic polymer.

4. The oral solid dosage form according to claim 1, wherein said cationic polymer and said anionic polymer are present in a ratio of about 1:9 to about 9:1.

5. The oral solid dosage form according to claim 4, wherein said ratio is 1:1.

6. The oral solid dosage form according to claim 1, further comprising at least one bioactive agent chosen from a protein, a protein association, a peptide, a drug, a pro-drug, an anti-oxidant, an anti-tumoral agent, an anti-inflammatory agent, a bacteria, a probiotic, or combinations thereof.

7. The oral solid dosage form according to claim 1, wherein the total amount of said enzyme in said dosage form is from about 3.3% to about 90%.

8. The oral solid dosage form according to claim 1, wherein said isolated histaminase enzyme and said isolated catalase enzyme are present in a ratio of about 1:1 to about 2:1.

9. The oral solid dosage form according to claim 6, wherein said drug is a non-steroidal anti-inflammatory drug (NSAID), and/or a histamine antagonist (antihistamine).

10. The oral solid dosage form according to claim 9, wherein said non-steroidal anti-inflammatory drug (NSAID) is chosen from ibuprofen, naproxen, benoxaprofen, flurbiprofen, fenoprofen, fenbuprofen, ketoprofen, loxoprofen, pranoprofen, carprofen, oxoprofen, microprofen, tioxaprofen, suprofen, alminoprofen, fluprofen, aspirin, diflunisal, salsalate, olsalazine, sulfasalazine, indomethacin, sulindac, etodolac, ketorolac, diclofenac, mefenamic acid, meclofenamic acid, flufenamic acid, tolfenamic acid, celecoxib, valdecoxib, rofecoxib, etoricoxib or the combination thereof, and said histamine antagonist (antihistamine) is a H1-receptor antagonist chosen from Cetirizine, Chlorpheniramine, Clemastine, Desloratadine, Dexchlorpheniramine, Dimenhydrinate, Dimetindene, Diphenhydramine, Doxylamine, Ebastine, Embramine, Fexofenadine, Levocetirizine, Loratadine, Meclozine, Olopatadine, Pheniramine, Promethazine, Quetiapine, or combinations thereof and/or a H2-receptor antagonist chosen from Cimetidine, Famotidine, Lafutidine, Nizatidine, Ranitidine, Roxatidine.

11. A method of treating an enteric disease comprising administering to a subject in need thereof an oral solid dosage form according to claim 1, wherein said enteric disease is selected from the group consisting of an inflammatory disease, a food induced histaminosis or combination thereof.

12. The method according to claim 11, wherein said inflammatory disease is Crohn's disease, ulcerative colitis, collagenous colitis, lymphocytic colitis, ischemic colitis, diversion colitis, Behçet's disease, indeterminate colitis, or combination thereof.

13. The intestinal delivery composition of claim 1, further comprising a coating.

14. The intestinal delivery composition of claim 13, wherein said coating comprises a compound chosen from hydroxypropylmethylcellulose phthalate, hydroxypropylmethylcellulose acetate succinate, ethylcellulose, and a methacrylate copolymer with carboxylic groups.

* * * * *